United States Patent
Susín Arrieta

(10) Patent No.: US 8,648,233 B2
(45) Date of Patent: Feb. 11, 2014

(54) HYBRID ARTICHOKE VARIETY NUN 4021 AR

(75) Inventor: Ignacio Susín Arrieta, Huesca (ES)

(73) Assignee: Nunhems B.V., Nunhem (NL)

( * ) Notice: Subject to any disclaimer, the term of this patent is extended or adjusted under 35 U.S.C. 154(b) by 425 days.

(21) Appl. No.: 12/886,181

(22) Filed: Sep. 20, 2010

(65) Prior Publication Data

US 2011/0072536 A1 Mar. 24, 2011

(51) Int. Cl.
*A01H 5/00* (2006.01)
*A01H 5/10* (2006.01)
*A01H 1/00* (2006.01)
*C12N 15/82* (2006.01)

(52) U.S. Cl.
USPC .......... 800/298; 800/260; 800/268; 800/276; 435/410

(58) Field of Classification Search
None
See application file for complete search history.

(56) References Cited

U.S. PATENT DOCUMENTS

2009/0044299 A1  2/2009  Colfer

FOREIGN PATENT DOCUMENTS

| WO | WO 2006/108697 | 10/2006 |
|---|---|---|
| WO | WO 2007/128559 | 11/2007 |

OTHER PUBLICATIONS

PVP 9000179 (Plant Variety Protection No. 9000179, Jan. 31, 1991).*
Calabrese et al., "Yield And Quality Of New Commercial Seed Grown Artichoke Hybrids," Acta Horticulturae, vol. 660, pp. 77-82 (2004).
Martin et al, "Identification of Markers linked to Agronomic Traits in Globe Artichoke," Australian Journal of Crop Science, vol. 1, No. 2, pp. 43-46 (2008).
Meyer and Stasse-Wolthuis, "The Bifidogenic Effect of Insulin and Oligofructose and its Consequences for Gut Health," European Journal of Clinical Nutrition, vol. 63, pp. 1277-1289 (2009).
Pecaut et al., "Intérêt des plants sains d'artichaut régénées par la culture in Vitro," Revue Horticole, vol. 256, pp. 21-26 (1985).
Pisanu et al., "Yield And Biometric Characteristics Of 9 Clones Selected From The Population Of 'Spinoso Sardo' Artichokes," Acta Horticulturae, vol. 660, pp. 83-89 (2004).
Ryder t al., "The Globe Artichoke (*Cynara scolymus* L)," Horticultural Science, vol. 18, pp. 646-653 (1983).
Schrader, "Growth Regulator Gives Earlier Harvest in Artichokes," California Agriculture, vol. 48, No. 3, pp. 29-32 (1994).
Smith et al., "Artichoke Production in California," University of California, Division of Agriculture and Natural Resources, Publication No. 7221 (1997).
Vos et al., "AFLP: A New Technique for DNA fingerprinting," Nucleic Acid Research, vol. 23, pp. 4407-4414 (1995).
Decision of the Dutch Board for Plant Varieties to grant of a Dutch Breeder's right for Opera; May 31, 2012; see pp. 1-2 and 9-12 (of 14).

\* cited by examiner

*Primary Examiner* — Shubo (Joe) Zhou
*Assistant Examiner* — Keith Robinson
(74) *Attorney, Agent, or Firm* — Hunton & Williams LLP

(57) ABSTRACT

The invention provides a new and distinct hybrid variety of globe artichoke, NUN 4021 AR or Opera F1, which is characterized by producing high quality, purple heads for the fresh market and/or the processing industry.

26 Claims, No Drawings

HYBRID ARTICHOKE VARIETY NUN 4021 AR

FIELD OF THE INVENTION

The present invention relates to the field of plant breeding. In particular, the invention provides for a new and distinct hybrid variety of Globe artichoke designated NUN 4021 AR (or "Opera F1"). The new variety produces medium sized heads, suitable for both the fresh market and/or the processing market. The variety is medium-early in time of appearance of the floral heads. The heads have outer bracts which are mainly purple and a triangular/conical shape (in the longitudinal section). The variety is distinct from the most similar hybrid variety, Concerto F1, by the significantly earlier time of appearance of the central flower head and significantly fewer days to first harvest (earliness), significantly more axillary shoots being produced and primary and secondary flower heads being smaller and weighing significantly less compared to heads of Concerto F1 at harvest stage. Provided are seeds of NUN 4021 AR, plants and plant parts produced from these seeds (such as heads, hearts, bottoms, etc.), vegetative reproductions of the variety NUN 4021 AR, and progeny of the variety.

SUMMARY OF THE PREFERRED EMBODIMENTS OF THE INVENTION

The invention provides for a new hybrid variety of Globe artichoke called NUN 4021 AR. The invention also provides for a plurality of seeds of the new variety, plants produced from growing the seeds and plant parts obtainable from the grown plant, such as (harvested) flower heads, or parts of the flower heads (e.g., hearts, bottoms, etc).

Thus, in one aspect, the invention provides for seeds of artichoke variety designated NUN 4021 AR, wherein a representative sample of seeds of said variety was deposited under Accession Number NCIMB 42085.

In another aspect, the invention provides for an artichoke plant of artichoke variety NUN 4021 AR, a representative sample of seed from said variety has been deposited under Accession Number NCIMB 42085.

In other aspects, the invention provides for plant parts, such as pollen, flower heads, hearts, bottoms, bracts, shoots, cuttings, and receptacles of variety NUN 4021 AR, or parts thereof.

In other aspects, the invention provides for progeny of variety NUN 4021 AR such as progeny obtained by selfing NUN 4021 AR one or more times and/or cross-pollinating NUN 4021 AR with another Globe artichoke plant or variety one or more times. In particular, the invention provides for progeny that retain all the morphological and physiological characteristics of NUN 4021 AR when grown under the same environmental conditions. In another aspect, the invention provides for vegetative reproductions of the variety and essentially derived varieties (EDVs) of NUN 4021 AR.

DETAILED DESCRIPTION OF THE PREFERRED EMBODIMENTS

Definitions

"Artichoke" or "Globe artichoke" refers herein to plants of the species Cynara scolymus L. (synonym Cynara cardunculus var. scolymus L.)

"Flower head" or "head" refers to immature flower heads (also called "flower buds" or "capitulates"), harvested or on the plant. The "central flower head" refers to the terminal flower head produced on the central, main stem. Other flower heads are produced on lateral branches.

"Heart" is the edible part of the flower head comprising or consisting of the fleshy receptacle (or a part thereof) with the fleshy base of the inner bracts (or parts thereof). "Artichoke bottom" is the edible fleshy lower part of the heart (receptacle).

"UPOV descriptors" are the plant variety descriptors described for Globe Artichoke in the "Guidelines for the Conduct of Tests for Distinctness, Uniformity and Stability," TG/184/3 (Geneva 2001), as published by UPOV (International Union for the Protection of New Varieties and Plants, available on the world wide web at upov.int) and which can be downloaded from the world wide web at upov.int/en/publications/tg_rom/tg_index.html, and is herein incorporated by reference in its entirety.

As used herein, the term "plant" includes the whole plant or any parts or derivatives thereof, preferably having the same genetic makeup as the plant from which it is obtained, such as plant organs (e.g., harvested or non-harvested heads, hearts, receptacles), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants (e.g., harvested tissues or organs), such as plant cuttings, vegetative propagations, embryos, pollen, ovules, fruits, flowers, leaves, seeds, clonally propagated plants, roots, stems, root tips, grafts, parts of any of these and the like. Also any developmental stage is included, such as seedlings, cuttings prior or after rooting, mature plants or leaves.

"Harvested plant material" refers herein to plant parts (e.g., heads detached from the whole plant or hearts removed from the heads) which have been collected for further storage and/or further use.

"Harvested seeds" refers to seeds harvested from a line or variety, e.g., produced after self-fertilization or cross-fertilization and collected.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) is a variety (i.e., shall be deemed to be essentially derived from another variety, "the initial variety") when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained, for example, by the selection of a natural or induced mutant, or of a somaclonal variant, the selection of a variant individual from plants of the initial variety, backcrossing, or transformation by genetic engineering.

"Plant line" is, for example, a breeding line which can be used to develop one or more varieties.

"Hybrid variety" or "F1 hybrid" refers to the seeds harvested from crossing two inbred parental lines. For example, the (male-sterile) female parent is pollinated with pollen of the male parent to produce hybrid (F1) seeds on the female parent.

"Average" refers herein to the arithmetic mean.

Globe artichoke is a vegetable crop originating from the Mediterranean region. The immature flower heads (also called "globes") contain edible parts, the fleshy bracts and hearts, which can be harvested for the fresh market or for industrial purposes (e.g., the canning industry). Certain extracts are also used in the pharmaceutical field.

Artichoke is predominantly cross-pollinating (due to the stigmatic surfaces maturing several days after pollen shedding) and selfing can result in some inbreeding depression. Artichoke cultivars have traditionally been bred as clones, using vegetative propagation (planting of basal stumps or suckers), because seed populations were not uniform enough for cultivation. In recent years seed propagated hybrid cultivars have been developed which do have good uniformity, such as Madrigal F1, Concerto F1 and others. These hybrids are produced from true breeding inbred parental lines.

The shift to seed-planted varieties (rather than vegetative cultivation) has enabled artichoke to be grown as an annual crop, although seed-planted varieties can also be grown as perennials. Seed-planted varieties are cost and labor saving, because seeds are sown mechanically. Also yields and quality are much higher, probably to some extent due to the fact that direct-seeded plants produce long taproots, which penetrate deeper into the soil than the vegetative plantations. Hybrid vigor also plays a role in improved yields, as does the better pest and disease control of annually seeded crops. Although a number of (seed-planted) hybrid varieties exist, there is still a need for new, high yielding, uniform hybrids with good head quality.

A number of characteristics are important to artichoke breeders including (a) the time of harvest (varieties adapted to early or late harvest); (b) the size and quality of the heads (determining whether the heads are suitable for fresh and/or industry purposes); (c) the shape of the heads; (d) the size of the plant; and (e) the spinelessness of the bracts.

The present invention provides a new purple-headed hybrid variety, NUN 4021 AR, which is relatively early maturing and produces heads suitable for both the fresh market and/or the processing industry, but most suitable for the fresh market. The plants of NUN 4021 AR are most similar to the commercial variety Concerto F1, which is a purple-headed fresh market variety sold by Nunhems B.V. However, NUN 4021 AR differs from Concerto F1 in a number of characteristics and can easily be distinguished from Concerto F1 when grown under the same environmental conditions. First, the plants grown from NUN 4021 AR seeds are earlier in appearance of the central flower head than Concerto F1, which is a relatively late variety. Also the number of days from seeding to first harvest are at least about 10, 12, 13, 14 or 15 days (e.g., at least about 16, 17, 18 days) shorter for Opera F1 than for Concerto F1 when grown under the same conditions. In addition the number of axillary (lateral) shoots produced by NUN 4021 AR is significantly higher than for Concerto F1. The mature flower heads (primary and secondary) weigh significantly less and are significantly smaller in size (longitudinal length and diameter at the broadest point, also referred to as head base diameter). However, NUN 4021 AR has on average more secondary flower heads per plant than Concerto F1. Bract tightness (compactness) is somewhat less in NUN 4021 AR compared to Concerto F1, which has very compact bracts. Other differences can be seen in the Examples, e.g., in Table 3, 4, 5 and 6.

Compared to Symphony F1 (U.S. application Ser. No. 12/715,664), a green-headed hybrid variety of Nunhems B.V., NUN 4021 AR is slightly earlier in appearance and has a number of slightly different characteristics as shown in Table 2. Differences to Violet de Provence, Concerto F1 and Symphony F1 are also shown in Table 1.

NUN 4021 AR produces medium sized flower heads on the main stem and on lateral shoots. In the longitudinal section, the shape of the flower heads of NUN 4021 AR is triangular (also referred to as 'conical'). In addition, the leaf blade of NUN 4021 AR has a yellowish hue (in contrast to Symphony F1) and the central flower head has a rounded tip, while that of Symphony F1 is acute. The outer bracts are of NUN 4021 AR are slightly longer and broader than those of Symphony F1 and their emargination is slightly deeper. The outer bract color is mainly violet (compared to green for Symphony F1) and the inner bracts of the central flower head have more anthocyanin.

As discussed herein, one of the main differences between NUN 4021 AR (Opera F1) and Concerto F1 is the time of appearance of the central flower head, which is relatively late in Concerto F1 and "medium-early" in NUN 4021 AR, when grown under the same environmental conditions. The time of appearance of the central flower head correlates with the time to first harvest. If no giberellic acid ($GA_3$) is applied to the plants, then NUN 4021 AR is at least about 15 days (e.g., 16, 17 or 18 days) earlier than Concerto F1, i.e., the first harvest is earlier. $GA_3$ is a plant growth regulator which can be applied one or more times to artichoke plants to initiate and/or advance bolting, bud formation and therefore harvest time (see, e.g., Wayne L. Schrader, California Agriculture 48(3): 29-32, "Growth regulator gives earlier harvest in artichokes."). By, for example, combining production of non-$GA_3$ treated plants with $GA_3$ treated plants, harvest time and harvest period can be optimally controlled. This way, different field plots may be treated at different times, to provide enable harvest in intervals. In one embodiment, NUN 4021 AR, or derivatives or progeny thereof, may be cultivated and treated one or more times with $GA_3$, e.g., as described in Calabrese et al. ISHS 2004, Acta Hort. 660: 77-82.

NUN 4021 AR is typically sown in the USA between October and June, with harvest almost all year round. The variety has a reduced vernalization (chilling) requirement. NUN 4021 AR can be grown as an annual (recommended) and perennial crop.

The outer bracts of the flower heads are mainly purple and with no or a few small spines in both Symphony F1 and NUN 4021 AR and have a thick base. A mucron is lacking in both. Receptacles are similar between these two varieties, with a medium thickness. Heads of both are relatively compact (dense), with a high number of internal bracts.

Another variety which is similar to NUN 4021 AR is a vegetatively propagated variety called Violet de Provence. However, this variety is not a hybrid, has lesser yield and can also be distinguished easily from NUN 4021 AR when grown under the same environmental conditions. The most obvious distinction is that the leaves of Violet de Provence are "entire" (not lobed). Other differences are the way of multiplication (clonal/vegetative versus seed-propagation) and earliness (time of appearance of the central flower head), with Violet de Provence being earlier. NUN 4021 AR has higher yields and a better performance than Violet de Provence, especially under stress conditions (e.g., soil and/or water salinity, cold stress, etc.). NUN 4021 AR also produces better field uniformity (fewer dead plants after planting) and healthier fields.

The morphological and/or physiological differences between NUN 4021 AR and other known varieties can easily be established by growing NUN 4021 AR next to the other varieties (in the same field, under the same environmental conditions), preferably in several locations which are suitable for artichoke cultivation, and measuring morphological and/or physiological characteristics of a number of plants (e.g., to calculate an average value and to determine the variation range/uniformity within the variety). Comparative varieties which can be grown in the same field are Concerto F1, Symphony F1 and others. These are commercially available. Seeds of Symphony F1 have also been deposited under ATCC number PTA-10654 of patent application U.S. Ser. No. 12/715,664.

For example, trials can be carried out in California, USA, whereby e.g., plant height, width, growth habit, side shoot number, foliage density, head size, head shape, head number, head texture, head fragrance, head weight, bract size, bract shape, bract texture, bract number, bract color, bract basal thickness, heart shape and size, heart color, papus length and color, head firmness, bract firmness, head gloss, leaf length and width, leaf incisions (serrations), leaf basal angle, leaf length to width ratio, leaf color, leaf texture, leaf venation, leaf basal thickness, distance between incisions, petiole length and width, pest and/or disease resistance/susceptibility can be measured and directly compared. Also post-harvest characteristics of heads can be compared, such as cold storage holding quality (browning), post-harvest oxidation of heads, and juiciness can be measured using known methods (see e.g., US 2009/0044299, paragraph 0016). The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (which can be found on the world wide web at rhs.org.uk/Plants/RHS-Publications/RHS-colour-charts).

Seeds of artichoke variety NUN 4021 AR are provided herein, wherein a representative sample of said seeds (2500 seeds) has been deposited, under the Budapest Treaty, with Accession Number NCIMB 42085.

Seeds of NUN 4021 AR are obtainable by crossing the male parent with the male-sterile female parent and harvesting the seeds produced on the female parent. The resultant NUN 4021 AR seeds can be grown to produce NUN 4021 AR plants. In one embodiment, a plurality of NUN 4021 AR seeds are packaged into small and/or large containers (e.g., bags, cartons, cans, etc.). The seeds may be treated with various compounds, such as seed coatings.

Also provided are plants of artichoke variety NUN 4021 AR, or a part thereof, produced from seeds, wherein a representative sample of said seeds has been deposited under Accession Number NCIMB 42085. Plants of NUN 4021 AR can be produced by seeding directly in the ground (e.g., field) or by germinating the seeds in controlled environment conditions (e.g., greenhouses) and then transplanting the seedlings into the field. (See Smith et al., University of California, Division of Agriculture and Natural Resources publication 7221, "Artichoke Production in California," and the world wide web at anrcatalog.ucdavis.edu for cultivation, harvesting, handling and postharvest methods commonly used).

Parts of NUN 4021 AR encompass any cells, tissues, organs obtainable from the seedlings or plants, such as but not limited to: heads, hearts, bottoms, bracts, cuttings, pollen and the like. Such parts can be stored and/or processed further.

The invention also encompasses food or feed products comprising one or more of such parts, such as canned hearts or bottoms obtainable from NUN 4021 AR or from progeny thereof, or from a derived variety, such as an EDV.

In a preferred embodiment, the invention provides for heads of artichoke variety NUN 4021 AR, or a part of the head. The heads are preferably harvest-stage heads. They may be harvested (e.g., manually, by removing the heads from the remaining plant) and stored and/or processed further. In another embodiment, the invention provides for a container comprising or consisting of a plurality of harvested heads of NUN 4021 AR, or progeny thereof, or a derived variety, such as an EDV.

In yet a further embodiment, the invention provides for a method of producing a new artichoke plant. The method comprises crossing NUN 4021 AR, either as male or as female parent, with a second artichoke plant (or a wild relative of artichoke) one or more times, and/or selfing NUN 4021 AR one or more times, and selecting progeny from said crossing and/or selfing. Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g., the F2) with another artichoke plant (and/or with a wild relative of artichoke). Using common breeding methods such as backcrossing or recurrent selection, one or more specific characteristics may be introduced into NUN 4021 AR, to provide an EDV of NUN 4021 AR.

A "wild" relative of artichoke is herein selected from *Cynara cardunculus* var. *sylvestris* (wild cardoon), *Cynara cardunculus* subsp *cardunculus* (cultivated cardoon), *C. baetica, C. algarbiensis, C. syriaca, C. cornigera, C. cyrenaica, C. humilis* and *C. trournefortii*.

The invention provides for methods of producing varieties which retain all the morphological and physiological characteristics of NUN 4021 AR, or EDVs (Essentially Derived Varieties), which may differ from NUN 4021 AR in one, two, three or more morphological and/or physiological characteristics, but which are still genetically closely related to NUN 4021 AR. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 4021 AR if its DNA fingerprint is at least 80%, 90%, 95% or 98% identical to the fingerprint of NUN 4021 AR. In a preferred embodiment, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Pisanu et al. ISHS 2004, Acta Hort. 660).

By crossing and/or selfing also (one or more) single traits may be introduced into NUN 4021 AR (e.g., using backcrossing breeding schemes), while retaining the remaining morphological and physiological characteristics of NUN 4021 AR. For example, disease resistance genes may be introduced, genes responsible for one or more quality traits (such as head quality), yield, etc. Both single genes (dominant or recessive) and one or more QTLs (quantitative trait loci) may be transferred into NUN 4021 AR by breeding with NUN 4021 AR.

Any pest or disease resistance genes may be introduced into NUN 4021 AR, progeny thereof or into an EDV of NUN 4021 AR. Resistance to one or more of the following diseases is preferably introduced into plants of the invention: Powdery mildew, *Verticillium* wilt (*V. dahliae*), *Botrytis* rot, Curly Dwarf Virus and Bacterial Crown rot. Resistance to one or more of the following pests is preferably present or introduced into plants of the invention: artichoke plume moth (*Platyptilia caduidactyla*), artichoke moth (*Gortyna xantheses*), aphid resistance, proba bug resistance, two-spotted spider-mite resistance, Chrysanthemum leaf-miner, and Cribate weevil resistance. Other resistance genes, against pathogenic viruses (e.g., Artichoke Latent Virus, ArLV; artichoke mottled crinkle virus, AMCV; Tomato Spotted Wilt Virus, TSWV; Impatiens necrotic spot virus, INSV; Cucumber mosaic virus, CMV), fungi, bacteria or artichoke pests may also be introduced.

Thus, the invention also provides a method for developing an artichoke plant in an artichoke breeding program, using an artichoke plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 4021 AR or progeny thereof with a different artichoke plant, and wherein one or more offspring of the crossing are subject to one or more plant breeding techniques such as recurrent selection, backcrossing, pedigree breeding, mass selection, mutation breeding and genetic marker enhanced selection (see e.g., Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

In one embodiment, NUN 4021 AR may also be mutated (by e.g., irradiation, chemical mutagenesis, heat treatment, etc.) and mutated seeds or plants may be selected in order to change one or more characteristics of NUN 4021 AR. Also natural mutants may be identified and used in breeding. Methods such as TILLING and/or EcoTILLING may be applied to artichoke populations in order to identify mutants. Similarly, NUN 4021 AR may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g., genes conferring pest or disease resistance, herbicide, fungicide or insecticide tolerance, etc.) can be introduced into NUN 4021 AR, or progeny thereof, by transforming NUN 4021 AR or progeny thereof with a transgene that confers the desired trait, wherein the transformed plant retains all the morphological and physiological characteristics of NUN 4021 AR or the progeny thereof and contains the desired trait.

The invention also provides for progeny of artichoke variety NUN 4021 AR obtained by further breeding with NUN 4021 AR. In one aspect, progeny are F1 progeny obtained by crossing NUN 4021 AR with another plant or S1 progeny obtained by selfing NUN 4021 AR. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have all the physiological and morphological characteristics of variety NUN 4021 AR when grown under the same environmental conditions. In another embodiment the progeny are EDVs and/or have one, two, or three distinct traits (qualitative or quantitative) introduced into NUN 4021 AR, while retaining all the other physiological and morphological characteristics of variety NUN 4021 AR when grown under the same environmental conditions.

The variety NUN 4021 AR, or its progeny (e.g., an EDV), can also be reproduced using vegetative reproduction methods. As such, the invention provides for a method of producing plants, or a part thereof, of variety NUN 4021 AR comprising vegetative propagation of variety NUN 4021 AR. Vegetative propagation comprises regenerating a whole plant from a part of variety NUN 4021 AR, such as a cutting, a cell culture or a tissue culture (e.g., in vitro meristem culture, see Pecaut et al. 1985, Revue Horticuole 256: 21-26), a "stump" (basal stem piece with attached root sections or a rooted section of the crown), suckers derived from NUN 4021 AR, offshoots derived from NUN 4021 AR or ovoli derived from NUN 4021 AR (see Ryder et al., 1983, Hort Science 18: 646-653).

The invention also provides for a vegetatively propagated plant of variety NUN 4021 AR, or a part thereof, having all the morphological and physiological characteristics of NUN 4021 AR when grown under the same environmental conditions.

The invention also provides for haploid plants and/or double haploid plants of NUN 4021 AR. Haploid and double haploid (DH) plants can, for example, be produced by anther or microspore culture and regeneration into a whole plant. For DH production chromosome doubling may be induced using known methods, such as colchicine treatment or the like.

Also provided are plant parts derived from variety NUN 4021 AR, or from a vegetatively propagated plant of NUN 4021 AR, being selected from the group consisting of: harvested flower heads or parts thereof, pollen, cells, leaves or parts thereof, petioles, shoots or parts thereof, stems or parts thereof, roots or parts thereof, cuttings, stumps, suckers, offshoots, ovoli, receptacles or parts thereof, bracts or parts thereof, flowers, florets, or flower buds.

Globe artichoke leaves represent a natural source of phenolic acids with dicaffeoylquinic acids, such as cynarin (1,3-dicaffeoylquinic acid), along with its biosynthetic precursor chlorogenic acid (5-caffeoylquinic acid) as the most abundant molecules. In various pharmacological test systems, artichoke leaf extracts have exhibited hepatoprotective, anticarcinogenic, antioxidative, antibacterial, anti-HIV, bile-expelling, and urinative activities as well as the ability to inhibit cholesterol biosynthesis and LDL oxidation. These broad therapeutic indications probably cannot be ascribed to a single, but to several active compounds that together generate additive or synergistic pharmacologic effects; these include mono- and dicaffeoylquinic acids, and flavonoids such as luteolin and its 7-O-glucoside. Artichoke tissues such as leaves, external bracts and stems can be used as a source of inulin and/or phenolics, useful for the production of food additives and nutraceuticals.

In one embodiment, the invention provides for extracts of a plant described herein and compositions comprising or consisting of such extracts. In a preferred embodiment, the extract consists of or comprises tissue of a plant described herein or is obtained from such tissue. For example, cynarin may be an extract obtained from leaf tissue and used to make a health-beneficial composition (e.g., a pharmaceutical composition or a food supplement). Likewise inulin (e.g., very long chain inulin, VLCI) may be extracted from globe artichoke tissue, such as roots and used in food or feed, food supplement, pharmaceutical or nutraceutical compositions. VCLI from Globe artichoke has health beneficial properties, e.g., on gut-health, see e.g. WO 2006/108697, WO2007/

128559 and Meyer and Stasse-Wolthuis, 2009 (European Journal of Clinical Nutrition 63, 1277-1289).

The invention also provides for a food or feed product comprising or consisting of a plant part described herein and/or an extract from a plant part described herein. The food or feed product may be fresh or processed, e.g., canned, steamed, boiled, fried, blanched and/or frozen, etc.

The invention also provides for containers such as cans, boxes, crates, bags, cartons, Modified Atmosphere Packagings, films (e.g., biodegradable films), etc. comprising plant parts of plants (fresh and/or processed) described herein.

Marketable heads are generally sorted by size and quality after harvest. Cartons may be packaged with "18s" (18 heads, each larger than 4.5 inches in diameter), "24s" (25 heads of 4-4.5 inches), "36s" (36 heads of 3.5-4 inches), "48$^{th}$" (48 heads of 3-3.5 inches) or "60s" (60 heads of 2.75-3 inches). The harvested heads of NUN 4021 AR are most suitable for packaging with 48$^{th}$ or 60s, see Examples regarding base head diameter of heads.

All documents (e.g., patent publications and applications) are herein incorporated by reference in their entirety.

EXAMPLES

Development of NUN 4021 AR

The hybrid NUN 4021 AR was developed from a clone of INRA (France) and a proprietary line of Nunhems obtained in Picanya, Spain. Inbred parental lines were developed from these lines through several generations of self-pollination and continued selection, e.g., for uniformity and earliness. The maternal inbred parent of NUN 4021 AR is a vegetative propagated proprietary line of Nunhems, which is male-sterile. The male inbred parent of NUN 4021 AR is a proprietary line of Nunhems propagated by seeds.

The female and male parents were crossed to produce hybrid (F1) seeds of NUN 4021 AR. The seeds of NUN 4021 AR can be grown to produce hybrid plants and parts thereof (e.g., flower heads). The hybrid NUN 4021 AR can be propagated by seeds or vegetative.

The hybrid variety is uniform and genetically stable. This has been established through evaluation of horticultural characteristics. Four independent hybrid seed production events resulted in no observable deviation in genetic stability. Coupled with the confirmation of genetic stability of the female and male parents the Applicant concluded that NUN 4021 AR is uniform and stable.

The hybrid has very good plant development and stress tolerance, good head quality and yield and is medium-early in appearance.

A total of 2500 seeds of the hybrid variety NUN 4021 AR (also called "Opera" or "Opera F1") were deposited by Nunhems B.V. on Dec. 3, 2012, at the NCIMB Ltd., Ferguson Building, Craibstone Estate, Bucksburn, Aberdeen AB21 9YA, United Kingdom (NCIMB). The deposit has been assigned Accession Number NCIMB 42085. A deposit of NUN 4021 AR and of the male parent line is also maintained at Nunhems B.V. The female parent line is also propagated and maintained vegetatively by Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Characteristics of NUN 4021 AR

Table 1 shows morphological and physiological distinguishing characteristics of NUN 4021 AR compared to similar varieties, Violet de Provence (a vegetatively propagated purple variety), Concerto F1 (a seed propagated purple hybrid variety sold by Nunhems B.V.), and Symphony F1 (a seed propagated green hybrid sold by Nunhems B.V.).

TABLE 1

| Morphological and Physiological Characteristic | Violet de Provence | Concerto F1 | Symphony F1 | NUN 4021 AR (Opera F1) |
|---|---|---|---|---|
| Leaf Incision | Incisions absent ("entire") | Incisions present (lobed) | Incisions present (lobed) | Incisions present (lobed) |
| Central flower head - time of appearance | Very early | late | Medium | Medium-early |
| Head color | purple | purple | green | purple |
| Propagation | vegetative | seed | seed | Seed |

Table 2 shows the UPOV descriptors of Symphony F1 (U.S. application Ser. No. 12/715,664) and NUN 4021 AR (Opera F1). Some of the most significant differences are highlighted in bold.

TABLE 2

| UPOV Number | UPOV descriptor | Symphony F1 | Opera F1 (NUN 4021 AR) |
|---|---|---|---|
| 1 | Plant: height (including central flower head) 3 = short, 5 = medium, 7 = tall | 7 | 7 |
| 2 | Plant: Number of lateral shoots on main stem 3 = few, 5 = medium, 7 = many | 6 | 6 |
| 3 | Main stem: height (excluding central flower head) 3 = short, 5 = medium, 7 = tall | 6 | 7 |
| 4 | Main stem: distance between central flower head and youngest well developed leaf | 5 | 5 |
| 5 | Main stem: diameter (at about 10 cm below central flower head) 3 = small, 5 = medium, 7 = large | 4 | 4 |
| 6 | Leaf: attitude (10-12 leaf stage) 1 = erect, 3 = semi-erect, 5 = horizontal | 3 | 3 |
| 7 | Leaf: long spines 1 = absent, 9 = present | 1 | 1 |
| 8 | Leaf: length 3 = short, 5 = medium, 7 = long | 7 | 6 |
| 9 | Leaf: incisions (10-12 leaf stage) 1 = absent, 9 = present | 9 | 9 |
| 10 | Leaf: number of lobes 3 = few, 5 = medium, 7 = many | 5 | 4 |
| 11 | Leaf: length of the longest lobe 3 = short, 5 = medium, 7 = long | 5 | 6 |
| 12 | Leaf: width of the longest lobe 3 = narrow, 5 = medium, 7 = broad | 6 | 6 |
| 13 | Lobe: shape of tip (excluding terminal lobe) 1 = acute, 2 = nearly right angle, 3 = obtuse | 2 | 2 |

TABLE 2-continued

| UPOV Number | UPOV descriptor | Symphony F1 | Opera F1 (NUN 4021 AR) |
|---|---|---|---|
| 14 | Lobe: Number of secondary lobes<br>1 = non or very few, 3 = few, 5 = medium, 7 = many, 9 = very many | 5 | 6 |
| 15 | Lobe: shape of tip of secondary lobes<br>1 = acuminate, 2 = acute, 3 = rounded | 3 | 3 |
| 16 | Leaf blade: shape in cross section<br>1 = flat, 2 = V-shaped | 2 | 2 |
| 17 | Leaf blade: intensity of green color (upper side)<br>3 = light, 5 = medium, 7 = dark | 5 | 5 |
| 18 | Leaf blade: hue of green color<br>1 = absent, 2 = yellowish, 3 = greenish | 1 | 2 |
| 19 | Leaf blade: intensity of grey hue<br>3 = weak, 5 = medium, 7 = strong | 3 | 3 |
| 20 | Leaf: hairiness on upper side<br>1 = absent or very weak, 3 = weak, 5 = medium, 7 = strong, 9 = very strong | 3 | 3 |
| 21 | Leaf blade: blistering<br>1 = absent or very weak, 3 = weak, 5 = medium, 7 = strong, 9 = very strong | 1 | 3 |
| 22 | Petiole: anthocyanin coloration at base<br>1 = absent or very weak, 3 = weak, 5 = medium, 7 = strong, 9 = very strong | 2 | 2 |
| 23 | Central flower head: length<br>3 = short, 5 = medium, 7 = long | 6 | 6 |
| 24 | Central flower head: diameter<br>3 = small, 5 = medium, 7 = large | 4 | 4 |
| 25 | Central flower head: size<br>3 = small, 5 = medium, 7 = large | 5 | 5 |
| 26 | Central flower head: shape in longitudinal section<br>1 = circular, 2 = broad elliptic, 3 = ovate, 4 = triangular, 5 = transverse broad elliptic | 4 | 4 |
| 27 | Central Flower head: shape of tip<br>1 = acute, 2 = rounded, 3 = flat, 4 = depressed | 1 | 2 |
| 28 | Central flower head: time of appearance<br>3 = early, 5 = medium, 7 = late | 5 | 4 |
| 29 | Central flower head: time of beginning of opening<br>3 = early, 5 = medium, 7 = late | 5 | 5 |
| 30 | First flower head on lateral shoot: length<br>3 = short, 5 = medium, 7 = long | 6 | 6 |
| 31 | First flower head on lateral shoot: diameter<br>3 = small, 5 = medium, 7 = large | 4 | 4 |
| 32 | First flower head on lateral shoot: size<br>3 = small, 5 = medium, 7 = large | 4 | 4 |
| 33 | First flower head on lateral shoot: shape in longitudinal section<br>1 = circular, 2 = broad elliptic, 3 = ovate, 4 = triangular, 5 = transverse broad elliptic | 4 | 4 |
| 34 | First flower head on lateral shoot: Degree of opening<br>3 = weak, 5 = medium, 7 = strong | 2 | 2 |
| 35 | Outer bract: length of base<br>3 = short, 5 = medium, 7 = long | 5 | 6 |
| 36 | Outer bract: width of base<br>3 = narrow, 5 = medium, 7 = broad | 5 | 6 |
| 37 | Outer bract: thickness at base<br>3 = thin, 5 = medium, 7 = thick | 7 | 7 |
| 38 | Outer bract: main shape<br>1 = broader than long, 2 = as broad as long, 3 = longer than broad | 3 | 3 |
| 39 | Outer bract: shape of apex<br>1 = acute, 2 = flat, 3 = emarginated | 3 | 3 |
| 40 | Outer bract: depth of emargination<br>3 = shallow, 5 = medium, 7 = deep | 4 | 5 |
| 41 | Outer bract: Color (external side)<br>1 = green, 2 = green striped with violet, 3 = violet striped with green, 4 = mainly violet, 5 = entirely violet | 1 | 4 |
| 42 | Outer bract: hue of secondary color (as 41)<br>1 = absent, 2 = bronze, 3 = grey | 1 | 1 |
| 43 | Outer bract: reflexing of tip<br>1 = absent, 9 = present | 1 | 1 |
| 44 | Outer bract: size of spine<br>1 = absent or very small, 3 = small, 5 = medium, 7 = large, 9 = very large | 1 | 1 |
| 45 | Outer bract: mucron<br>1 = absent, 9 = present | 1 | 1 |
| 46 | Central flower head: anthocyanin coloration of inner bracts<br>1 = absent or very weak, 3 = weak, 5 = medium, 7 = strong, 9 = very strong | 3 | 5 |
| 47 | Central flower head: density of inner bracts<br>3 = sparse, 5 = medium, 7 = dense | 6 | 6 |
| 48 | Receptacle: diameter<br>3 = small, 5 = medium, 7 = large | 3 | 4 |
| 49 | Receptacle thickness<br>3 = thin, 5 = medium, 7 = thick | 5 | 5 |
| 50 | Receptacle: shape in longitudinal section<br>1 = flat, 2 = slightly depressed, 3 = strongly depressed | 2 | 2 |
| 51 | Tendency to produce lateral shoots on base<br>3 = weak, 5 = medium, 7 = strong | 5 | 5 |

The most similar purple-headed variety is Concerto F1. Table 3 shows the variety NUN 4-21 AR (Opera F1) compared to Concerto F1 based on trial in Spain. Trial location: Nunhems Spain Breeding station in La Palma, Murcia (coordinates: 37°47'N, 0°57'W), Spain 2009-2010. Mild weather conditions. Planting date: Jul. 7, 2009. Drip irrigation. Two replication of 24 plants each, from which 10-20 plants or plant parts were randomly selected to measure characteristics.

TABLE 3

| Descriptor | Concerto F1 | OPERA F1 (NUN 4021 AR) |
|---|---|---|
| No. of days from seeding to first head harvest | 272 | 255 |
| Plant height (harvest stage) (cm) | 98.8 | 94.6 |
| Plant habit (harvest stage)<br>(1 = upright; 2 = Intermediate; 3 = Broad) | 1 | 1 |
| No. of axillary shoots (harvest stage) | 1.2 | 3.0 |
| Leaf (harvest stage) - spines<br>(1 = none; 2 = few; 3 = many) | 1 | 1 |
| Leaf (harvest stage) - blade length (cm) | 89.0 | 104.0 |
| Leaf (harvest stage) - blade width (cm) | 34.5 | 38.5 |
| Leaf (harvest stage) - shape<br>(1 = entire; 2 = slight lobed; 3 = deeply lobed) | 3 | 3 |

TABLE 3-continued

| Descriptor | Concerto F1 | OPERA F1 (NUN 4021 AR) |
|---|---|---|
| Leaf (harvest stage) - shape variability (1 = slight; 2 = moderate; 3 = high) | 2 | 2 |
| Primary flower head (harvest stage) - shape (1 = cylindrical; 2 = conical; 3 = ovoid; 4 = ellipsoid) | 2 | 2 |
| Primary flower head (harvest stage) - base diameter (cm) | 11.13 | 7.9 |
| Primary flower head (harvest stage) - length or depth (cm) | 11.74 | 9.31 |
| Primary flower head (harvest stage) - bract tightness (1 = Loose; 2 = moderately compact; 3 = compact) | 3 | 2 |
| Primary flower head (harvest stage) - bract luster (1 = dull; 2 = shiny) | 1 | 1 |
| Primary flower head (harvest stage) - external bract main color (1 = light green; 2 = mid green; 3 = dark green; 4 = purple; 5 = other) | 4 | 4 |
| Primary flower head (harvest stage) - external bract secondary color (1 = none; 2 = purple tint; 3 = brown tint; 4 = green tint; 5 = purple-brown tint; 6 = other) | 5 | 6 (yellowish) |
| Primary flower head (harvest stage) - location of secondary color (1 = tip; 2 = center; 3 = base; 4 = throughout) | 4 | 2 |
| Primary flower head (harvest stage) - internal bract color (1 = whitish-green; 2 = yellow-green; 3 = straw) | 2 | 2 |
| Primary flower head (harvest stage) - bract spines (1 = none; 2 = few; 3 = many) | 2 | 2 |
| Primary flower head (harvest stage) - bract shape (1 = round; 2 = oval; 3 = elongated) | 3 | 3 |
| Primary flower head (harvest stage) - bract tip shape (1 = entire; 2 = slightly notched; 3 = deeply notched) | 2 | 2 |
| Primary flower head (harvest stage) - bract length (mm) | 47.25 | 56.37 |
| Primary flower head (harvest stage) - bract width (mm) | 43.25 | 29.29 |
| Primary flower head (harvest stage) - peduncle diameter (mm) | 29.00 | 23.97 |
| Primary flower head (harvest stage) - weight per primary head (g) | 546.3 | 241.70 |
| Primary flower head (harvest stage) - no. of primary heads per plant | 1 | 1 |
| Secondary flower head - weight per secondary head (g) | 245.3 | 181.3 |
| Secondary flower head - no. secondary heads per plant | 3.25 | 3.6 |
| Floret color (1 = white; 2 = pink; 3 = red; 4 = purple; 5 = blue; 6 = other | 4 | 4 |
| Achene color (1 = monocolor; 2 = bicolor) | 2 | 2 |
| Achene color pattern (1 = solid; 2 = speckling; 3 = striping; 4 = other) | 2 | 2 |
| Achene primary color (1 = tan; 2 = brown; 3 = green; 4 = black; 5 = grey) | 5 | 1 |
| Achene secondary color (1 = tan; 2 = brown; 3 = green; 4 = black; 5 = grey) | 5 | 5 |

Statistical analysis (ANOVA) was carried out for three of the above traits:

1. Average number of days from seeding to first harvest (see Table 4)
2. Average head base diameter (seed Table 5)
3. Average weight of the primary head (see Table 6).

TABLE 4

Average number of days from seeding to first harvest

| | Average number of days from seeding to 1st harvest (standard deviation) | Sample size |
|---|---|---|
| Opera F1 | *254.53 (±3.25) | 15 |
| Concerto F1 | *272.4 (±4.97) | 15 |

*p-value = 0.000

The time of appearance from seeding to first harvest of Opera F1 is significantly earlier than that of Concerto F1. On average, the first harvest is about 17 to 18 days earlier for Opera F1 compared to Concerto F1. Concerto F1 is a late variety, while Opera F1 is a medium-early variety.

TABLE 5

Average head base diameter (diameter of the head at the broadest point)

| | Primary flower base diameter | Sample size |
|---|---|---|
| Opera F1 | *7.91 (±0.651) cm | 20 |
| Concerto F1 | *11.133 (±0.736) cm | 15 |

*p-value = 0.000

As can be seen, the base of the primary flower head is significantly smaller in Opera F1 compared to Concerto F1.

TABLE 6

Average primary head weight (grams)

| | Primary head weight (g) | Sample size |
|---|---|---|
| Opera F1 | *241.74 (±50.895) g | 20 |
| Concerto F1 | *546.333 (±44.777) g | 15 |

*p-value = 0.000

Opera F1 produces smaller primary heads than Concerto F1.

The invention claimed is:

1. A seed of artichoke variety NUN 4021 AR, wherein a representative sample of said seed has been deposited under Accession Number NCIMB 42085.

2. A plant of artichoke variety NUN 4021 AR, or a part thereof, wherein a representative sample of seed of said variety has been deposited under Accession Number NCIMB 42085.

3. A head of artichoke variety NUN 4021 AR, or a part thereof, produced from the plant of claim 2.

4. A method of producing an artichoke plant, comprising crossing the plant of claim 2 with a second artichoke plant one or more times, and selecting progeny from said crossing.

5. A method of producing an artichoke plant, comprising selfing the plant of claim 2 one or more times, and selecting progeny from said selfing.

6. The progeny of the plant of claim 2, wherein said progeny have all the physiological and morphological characteristics of variety NUN 4021 AR when grown under the same environmental conditions.

7. An Essentially Derived Variety of NUN 4021 AR having one, two or three physiological and/or morphological characteristics which are different from those of NUN 4021 AR and which otherwise has all the physiological and morphological characteristics of NUN 4021 AR, wherein a representative sample of seed of variety NUN 4021 AR has been deposited under Accession Number NCIMB 42085.

8. A method of producing plants, or a part thereof, of variety NUN 4021 AR comprising vegetative propagation of variety NUN 4021 AR, wherein a representative sample of seed of variety NUN 4021 AR has been deposited under Accession Number NCIMB 42085.

9. The method of claim 8, wherein said vegetative propagation comprises regenerating a whole plant from a part of variety NUN 4021 AR.

10. The method of claim 9, wherein said part is a cutting, a cell culture, a tissue culture, a stump, a sucker, a shoot, an offshoot or an ovoli.

11. A vegetative propagated plant of variety NUN 4021 AR, or a part thereof, having all the morphological and physiological characteristics of NUN 4021 AR when grown under the same environmental conditions, wherein a representative sample of seed of variety NUN 4021 AR has been deposited under Accession Number NCIMB 42085.

12. Plant parts derived from variety NUN 4021 AR, or from a plant of claim 11, wherein said plant part are harvested flower heads or parts thereof, pollen, cells, leaves or parts thereof, petioles, shoots or parts thereof, stems or parts thereof, roots or parts thereof, cuttings, stumps, offshoots, ovoli, receptacles or parts thereof, bracts or parts thereof, flowers, florets, or flower buds, wherein a representative sample of seed of variety NUN 4021 AR has been deposited under Accession Number NCIMB 42085.

13. A tissue of the plant of claim 2.

14. A tissue of the plant part of claim 12.

15. A food or feed product comprising a plant part of claim 12.

16. The food or feed product of claim 15, wherein said plant part is fresh or processed.

17. An artichoke plant produced by growing the seed of claim 1.

18. A method of producing an artichoke plant having a desired trait, comprising transforming the artichoke plant of claim 2 with a transgene that confers the desired trait, wherein the transformed plant retains all the phenotypic and morphological characteristics of variety NUN 4021 AR and contains the desired trait, a representative sample of seed of said variety NUN 4021 AR having been deposited under Accession Number NCIMB 42085.

19. An artichoke plant produced by the method of claim 18, wherein the plant comprises the desired trait and all of the physiological and morphological characteristics of NUN 4021 AR.

20. A method of introducing a single locus conversion into NUN 4021 AR comprising
(a) crossing a plant of variety NUN 4021 AR, a representative sample of seed of said variety having been deposited under Accession Number NCIMB 42085, with a second plant comprising a desired single locus to produce F1 progeny plants;
(b) selecting F1 progeny plants that have the single locus to produce selected F1 progeny plants;
(c) crossing the selected progeny plants with at least a first plant of NUN 4021 AR to produce backcross progeny plants;
(d) selecting backcross progeny plants that have the single locus and physiological and morphological characteristics of NUN 4021 AR to produce selected backcross progeny plants; and
(e) repeating steps (c) and (d) one or more times in succession to produce selected second or higher backcross progeny plants that comprise the single locus and otherwise comprise all of the physiological and morphological characteristics of NUN 4021 AR when grown in the same environmental conditions.

21. The method of claim 20, wherein the single locus confers a trait, wherein the trait is pest resistance or disease resistance.

22. The method of claim 21, wherein the trait is disease resistance and the resistance is conferred to powdery mildew, *Verticillium* wilt, *Botrytis* rot, Curly Dwarf Virus, or Bacterial Crown rot.

23. The method of claim 21, wherein the trait is pest resistance and the resistance is conferred to artichoke plume moth, artichoke moth, aphid resistance, proba bug resistance, two-spotted spider-mite resistance, Chrysanthemum leaf-miner, or Cribate weevil.

24. A cell or tissue culture produced from a plant of claim 2.

25. An artichoke plant regenerated from a cell or tissue culture of claim 24, said plant expressing all the morphological and physiological characteristics of NUN 4021 AR, wherein a representative sample having been deposited under Accession Number NCIMB 42085.

26. The Essentially Derived Variety of claim 7, wherein said Essentially Derived Variety is obtained by the selection of a natural or induced mutant, or of a somaclonal variant; the selection of a variant individual from plants of the initial variety, backcrossing, or transformation by genetic engineering.

* * * * *